United States Patent [19]

Kuribara et al.

[11] Patent Number: 4,989,570
[45] Date of Patent: Feb. 5, 1991

[54] FAIL DETECTING SYSTEM FOR SENSOR MONITORING CONCENTRATION OF A FUEL IN BLENDED MULTI-FUEL FOR INTERNAL COMBUSTION ENGINE AND FAIL-SAFE SYSTEM IN LAMBDA-CONTROL

[75] Inventors: Masaru Kuribara; Masamichi Imamura; Yoshiki Yuzuriha, all of Gunma, Japan

[73] Assignee: Japan Electronic Control Systems Co., Ltd., Isezaki, Japan

[21] Appl. No.: 510,694

[22] Filed: Apr. 19, 1990

[30] Foreign Application Priority Data

Apr. 19, 1989 [JP] Japan ............................ 1-45871[U]
Jul. 11, 1989 [JP] Japan ................................ 1-178222

[51] Int. Cl.$^5$ ...................... F02B 75/12; F02D 41/04; G01M 19/00; G01F 25/00
[52] U.S. Cl. .................................. 123/494; 123/1 A; 123/479; 73/118.1; 73/304 C
[58] Field of Search ............... 123/1 A, 381, 478, 479, 123/491, 494, 575, 576, 577, 578; 73/116, 117.2, 117.3, 118.1, 119 R, 119 A, 304 C; 364/550

[56] References Cited

U.S. PATENT DOCUMENTS

| 4,594,968 | 6/1986 | Degobert et al. | 123/494 X |
|---|---|---|---|
| 4,706,630 | 11/1987 | Wineland et al. | 123/494 X |
| 4,764,884 | 8/1988 | Noyori | 123/494 X |
| 4,770,129 | 9/1988 | Miyata et al. | 123/494 X |
| 4,817,418 | 4/1989 | Asami et al. | 83/118.1 |
| 4,825,691 | 5/1989 | Sekiguchi | 73/118.1 |
| 4,836,016 | 6/1989 | Nakano et al. | 73/118.1 |
| 4,905,655 | 3/1990 | Maekawa | 123/494 |
| 4,909,225 | 3/1990 | Gonze et al. | 123/494 |
| 4,913,099 | 4/1990 | Ota | 123/494 X |
| 4,942,848 | 7/1990 | Terasaka | 123/494 X |

Primary Examiner—Willis R. Wolfe
Attorney, Agent, or Firm—Foley & Lardner, Schwartz, Jeffery, Schwaab, Mack, Blumenthal & Evans

[57] ABSTRACT

A fail-detection system is designed for detecting failure of a fuel concentration sensor for monitoring concentration of one of a plurality of different types of fuels which are blended to be supplied to an internal combustion engine, which fuel concentration sensor varies output signal level depending upon the monitored fuel concentration in the blended fuels. The system comprises first means for receiving the output signal from the fuel concentration sensor for providing a monitored data associated with monitored fuel concentration, second means for providing a reference data representative of normal range of the value of the monitored data, and third means for comparing the monitored data with the reference data for detecting abnormality of the fuel concentration sensor when the monitored data is out of a predetermined relationship with the reference data.

16 Claims, 9 Drawing Sheets

FAIL DETECTING SYSTEM FOR SENSOR MONITORING CONCENTRATION OF A FUEL IN BLENDED MULTI-FUEL FOR INTERNAL COMBUSTION ENGINE AND FAIL-SAFE SYSTEM IN LAMBDA-CONTROL

BACKGROUND OF THE INVENTION

1. Field of the Invention

The present invention relates generally to a fuel supply control system for an internal combustion engine which is driven with a blended fuel composed of a plurality of mutually different fuels, such as gasoline and alcohol. More specifically, the invention relates to a fail detection of failure of a sensor for monitoring blending ratio of one of fuel, and fail-safe system for feedback control (λ-control) of air/fuel ratio upon occurrence of failure of the blending ratio sensor.

2. Description of the Background Art

For anti-pollution purpose, various attempt has been made for using non-gasoline or gasoline containing mixture fuel for reducing amount of $No_x$, CO and other pollutant. Typical blended fuel is gasoline/alcohol mixture. As will be appreciated, because of difference of octane value and combusibility of respective invidual fuels, fuel injection amount and spark ignition timing and so forth has to be adapted for the blending ratio of the fuels.

In case of pure gasoline, it has been considered that stoichiometric air/fuel is 15:1. On the other hand, stoichiometric air/fuel ratio in case of pure alcohol, e.g. methanol, is 5:1. Therefore, desired air/fuel ratio in the blended fuel is differentiated significantly depending upon blending ratio of the alcohol versus gasoline. Therefore, for precisely controlling fuel supply amount for the engine, it becomes essential to detect the alcohol ratio in the blended fuel so that stoichiometric or target air/fuel ratio can be precisely determined.

Various alcohol sensors have been proposed and put in the market for use in such purpose. Precision of monitored result of alcohol ratio in the blended fuel is important factor for determining precision level of the fule supply control, because of substantial variation of the desired or target air/fuel ratio for obtaining optimal engine performance. In other words, failure of the alcohol sensor in such fuel supply control system will become critical for such type of engine control.

SUMMARY OF THE INVENTION

Therefore, it is an object of the present invention to provide a fail detection system for detecting failure of a blending ratio sensor for monitoring concentration of selected one of a plurality of fuels in a blended fuel.

Another object of the present invention is to provide a fail-safe system in a feedback control system for air/fuel ratio of an air/fuel mixture to be introduced into an engine combustion chamber.

According to one aspect of the invention, a fail-detection system for a fuel concentration sensor for monitoring concentration of one of a plurality of different types of fuels which are blended to be supplied to an internal combustion engine, which fuel concentration sensor vaires output signal level depending upon the monitored fuel concentration in the blended fuels, the system comprises:

first means for receiving the output signal from the fuel concentration sensor for providing a monitored data associated with monitored fuel concentration;

second means for providing a reference data representative of normal range of the value of the monitored data; and third means for comparing the monitored data with the reference data for detecting abnormality of the fuel concentration sensor when the monitored data is out of a predetermined relationship with the reference data.

Preferably, the first means samples the output signal of the fuel concentration sensor with a given interval as the monitored data, the second means provides first reference data representative of a predetermined allowable maximum value of the monitored data and a second reference data representative of a predetermined allowable minimum value of the monitored data, and the third means detects abnormality of the fuel concentration sensor when the monitored data value is out of an allowable range defined by the first and second reference data. In such case, the first reference data may be set at a possible monitored data value when the concentration of the fuel to be monitored is 100% and the second reference data may be set at a possible monitored data value when trhe concentration of the fule ti be monitored is 0%.

In the alternative, the first means may comprise a first peak hold means for sampling and holding upper peak value of the monitored data and a second peak hold circuit means for sampling and holding lower peak value of the monitored data, and the first means includes a difference deriving means for deriving a difference data of the upper peak value and the lower peak value, the second means provides the reference data representative of an allowable maximum difference value, and the third means compares the difference data with the reference data to detect abnormality of the fuel concentration sensor when the difference data is greater than the reference data.

According to another aspect of the invention, a fail-detection system for a fuel concentration sensor for monitoring concentration of one of a plurality of different types of fuels which are blended to be supplied to an internal combustion engine, which fuel concentration sensor vaires output signal level depending upon the monitored fuel concentration in the blended fuels, the system comprises:

first means sampling the output signal of the fuel concentration sensor with a given interval as the monitored data;

second means providing first reference data representative of a predetermined allowable maximum value of the monitored data and a second reference data representative of a predetermined allowable minimum value of the monitored data; and third means detecting abnormality of the fuel concentration sensor when the monitored data value is out of an allowable range defined by the first and second reference data.

According to a further aspect of the invention, a fail-detection system for a fuel concentration sensor for monitoring concentration of one of a plurality of different types of fuels which are blended to be supplied to an internal combustion engine, which fuel concentration sensor vaires output signal level depending upon the monitored fuel concentration in the blended fuels, the system comprises:

first means including a first peak hold means for sampling and holding upper peak value of the monitored data and a second peak hold circuit means for sampling and holding lower peak value of the monitored data, and a difference deriving means for deriving a difference data of the upper peak value and the lower peak value;

second means provides the reference data representative of an allowable maximum difference value; and third means compares the difference data with the reference data to detect abnormality of the fuel concentration sensor when the difference data is greater than the reference data.

In such case, the fail-detecting system may be active at initial stage of engine driving after a predetermined period of time from termination of engine cranking.

According to a yet further aspect of the invention, a fuel injection control system for an internal combustion engine for which a blended fuel composed of mutually different type of plurality of fuel is supplied for performing combustion, comprises:

a fuel injection system for injecting controlled amount of the blended fuel to an induction system of the engine for forming an air/fuel mixture to be combustioned in a combustion chamber of the engine;

first means for monitoring basic fuel injection control parameter for deriving a basic fuel injection amount on the basis thereof;

second means for monitoring preselected fuel injection amount correcting parameter for deriving a correction value for correcting the basic fuel injection amount;

third means for monitoring blending ratio of selected one of fuels in the blended fuel for deriving a blending ratio dependent correction value for correcting the basic fuel injection amount based thereon, the third means including a sensor for monitoring concentration of the selected one of fuels;

fourth means for detecting abnormality of the sensor, including a monitoring data providing means for receiving the output signal from the fuel concentration sensor for providing a monitored data associated with monitored fuel concentration, a reference data providing means for providing a reference data representative of normal range of the value of the monitored data, and an abnormality detecting means for comparing the monitored data with the reference data for detecting abnormality of the fuel concentration sensor when the monitored data is out of a predetermined relationship with the reference data; and fifth means responsive to the fourth means detecting abnormality of the sensor for switching operational mode of the third means from normal mode in which the blending ratio dependent correction value on the basis of the monitored blending ratio, to a fail-safe mode in which the blending ratio dependent correction value is fixed at a given constant value.

The fuel injection control system may further comprise sixth means for detecting re-filling of fuel and the third means is responsive to the sixth means detecting re-filling of fuel for modifying the blending ratio dependent correction value in the fail-safe mode. In such case, the sixth means may monitor fuel level in a fuel tank for detecting re-filling of fuel on the basis of variation of the fuel level. In the alternative, the sixth means may detect opening of a fuel filler cap for detecting re-filling of fuel. Further more, the third means may modify the blending ratio depent correction value in the fail-safe mode in a magnitude variable depending upon a prediction of varaition of blending ratio by re-filling of fuel.

BRIEF DESCRIPTION OF THE DRAWINGS

The present invention will be understood more fully from the detailed description given herebelow and from the accompanying drawings of the preferred embodiment of the invention, which, however, should not be taken to limit the invention to the specific embodiment but are for explanation and understanding only.

In the drawings.

DESCRIPTION OF THE PREFERRED EMBODIMENT

Figure 1:
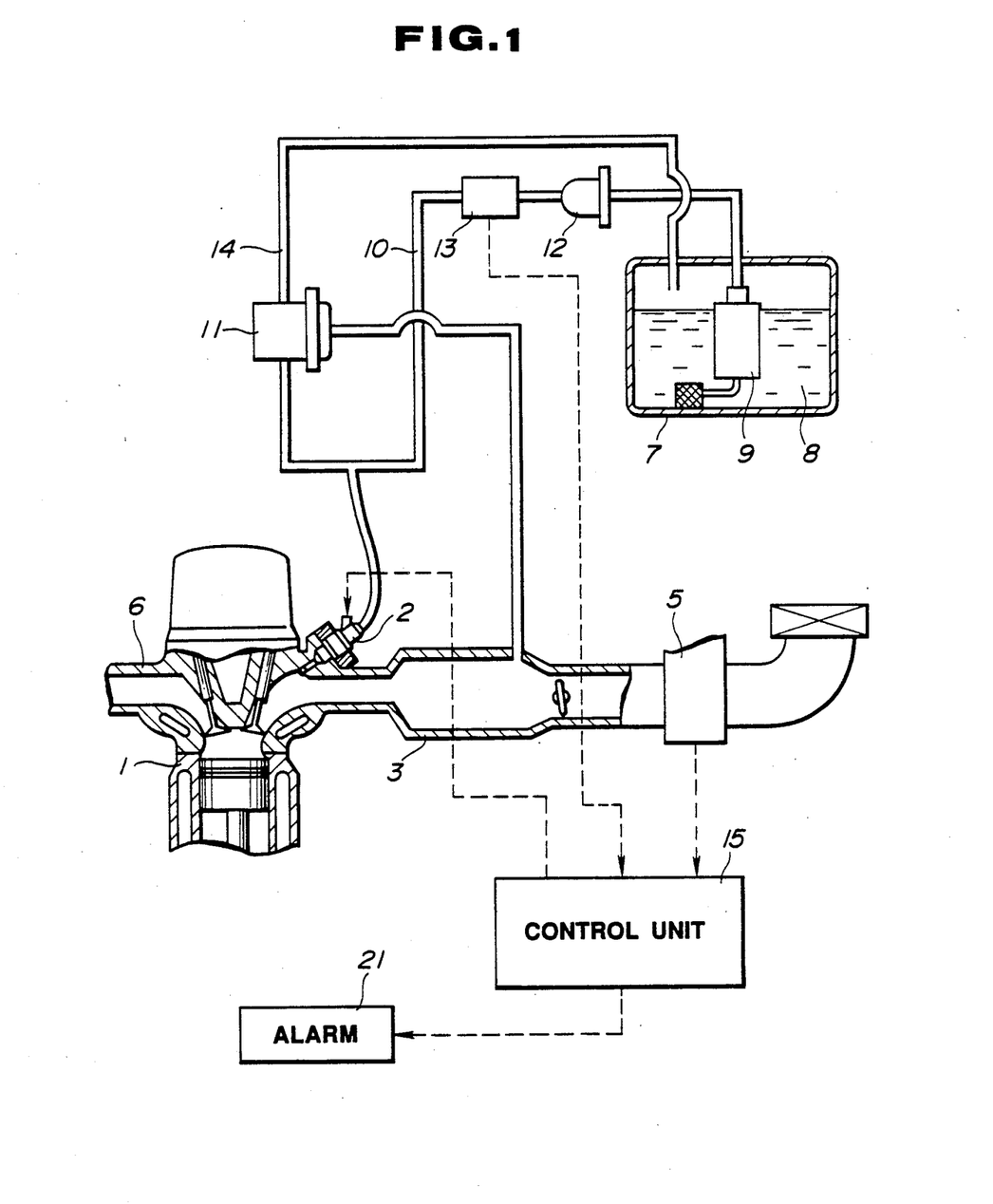
FIG. 1 is a schematic diagrammatical illustration of an internal combustion engine which is combasible with a gasoline/alcohol blended fuel at various alcohol blending ratio, and for which the preferred embodiment of a fail detection system and a fail-safe system for an air/fuel ratio feedback control system according to the present invention.

Referring now to the drawings, particularly to FIG. 1, a shown automotive intenal combustion engine 1 is designed for combustion with a blended fuel which is a mixture of gasoline and alcohol. For supplying the blended fuel, a fuel injection valve 2 is provided for injection controlled amount of the blended fuel into an intake manifold 3 of an air induction system, at a controlled timing. The fuel injection valve 2 is connected to a fuel supply circuit including a fuel tank 7 to which the blended fuel 8 is stored, a fuel pump 9 for sucking and pressurizing the fuel and feeding the fuel through a supply line 10. A fuel filter 12, an alcohol sensor 13 are provided in the supply line. The fuel circuit further include a return line 14 for returning excessive amount of the fuel to the fuel tank 8. For this purpose, a pressure regulator 11 is provided in the return line 14 to drain the excess level of fuel pressure through the return line.

Figure 6:
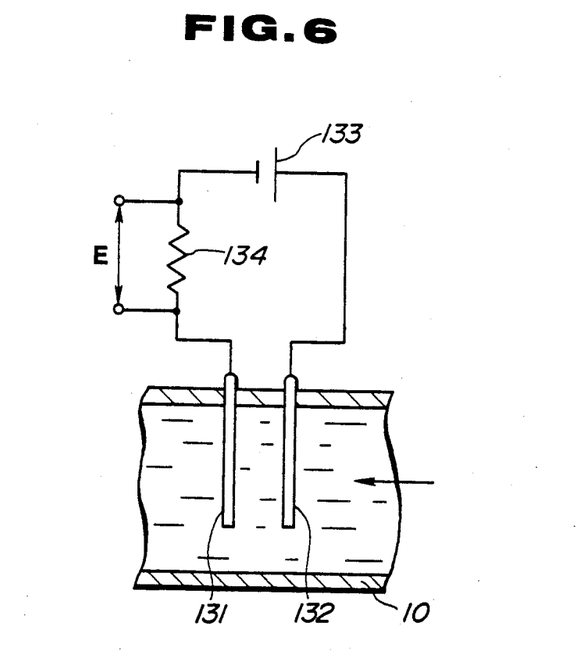
FIG. 6 is a fragmentary illustration of a one of typical constructions of alcohol sensors applicable for the fuel injection system of FIG. 2.

Various types of alcohol sensors may be employed in the shown fuel injection control system. FIG. 6 shows one typical construction of the alcohol sensor 13 for monitoring alcohol concentration (blended ratio in the fuel) by monitoring an electrical resistance between sensor electrodes. Therefore, the alcohol sensor of FIG. 6 has a pair of sensor electrodes 131 and 132 arranged within the supply line 10 in axially spaced relationship to each other by a predetermined or known distance. The pair of electrodes 131 and 132 are connected to positive and negative terminal of a vehicular battery 133 via a resister 134. The resister 134 serves as a voltage detector and thus detect output voltage e between jonctions E s between which the resistor 134 is provided.

Figure 7:
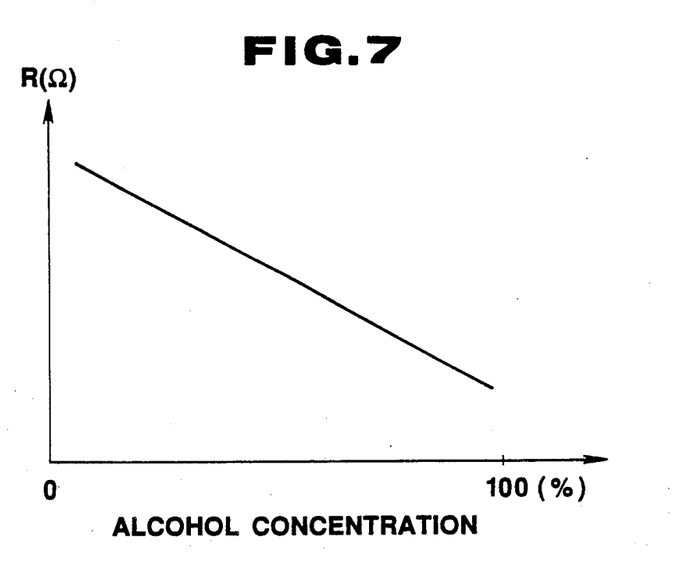
FIG. 7 is a chart showing variation of resistance between electrodes depending upon alcohol concentration.
Figure 8:
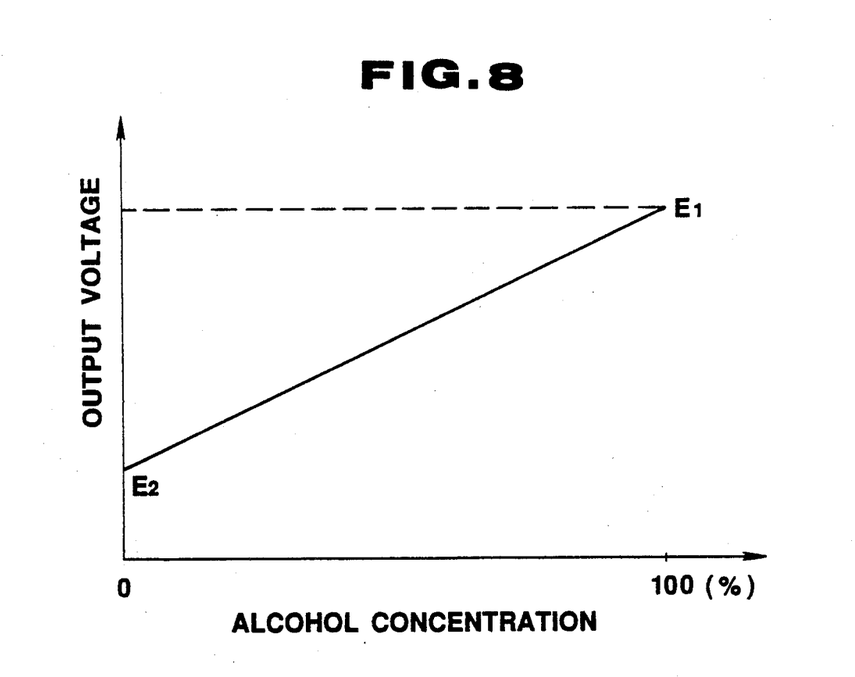
FIG. 8 is a chart showing eelationship between sensor output voltage and the alcohol concentration.

The alcohol sensor 13 with the shown construction monitors alcohol concentration of alcohol in the blended fuel to produce an alcohol concentration indicative signal, as shown in FIG. 8. As can be aware of from FIGS. 7 and 8, the alcohol concentration indicative signal is a voltage signal variable of the voltage level depending upon the concentration of the alcohol in the blended fuel supplied through the supply line 10. When the alcohol sensor 13 operates in normal state, the output voltage of the alcohol sensor as the alcohol concentration indicative signal varies between $E_1$ and $E_2$ while the alcohol concentration varies in a range of 0% (pure gasoline) to 100% (pure alcohol). The voltage level E of the alcohol concentration indicative signal of the alcohol sensor 13 is inversely proportional to the resistance $R\Omega$ between the electrodes 131 and 132.

An air flow meter 5 is provided between an air cleaner 4 and a throttle valve. The engine 1 also has an exhaust passage 6 for discharging an exhaust gas. The air flow meter 5 is of per se well known construction and any type of air flow meter can be employed in the shown fuel injection system. The air fuel meter 5 monitors air flow rate through the air induction system and supplies an air flow rate indicative signal as a data representative of an engine load condition. Though the shown embodiment employs the air flow meter for monitoring the engine load condition, the equivalent measurement of the engine load can be performed by various ways. For example, the intake vacuum, throttle valve open angle and so forth are data reflecting the engine load condition. Therefore, sensors any appropriate parameter representative of the engine load condition can be a replacement of the air flow meter in the shown embodiment. An oxygen sensor 6a (not shown in FIG. 1 but shown in FIG. 2) is provided in the exhaust passage 6. The oxygen sensor monitors oxygen concentration in the exhaust gas to produce a feedback signal λ representative of diviation of air/fuel ratio versus a predetermined stoichiometric value.

Figure 2:
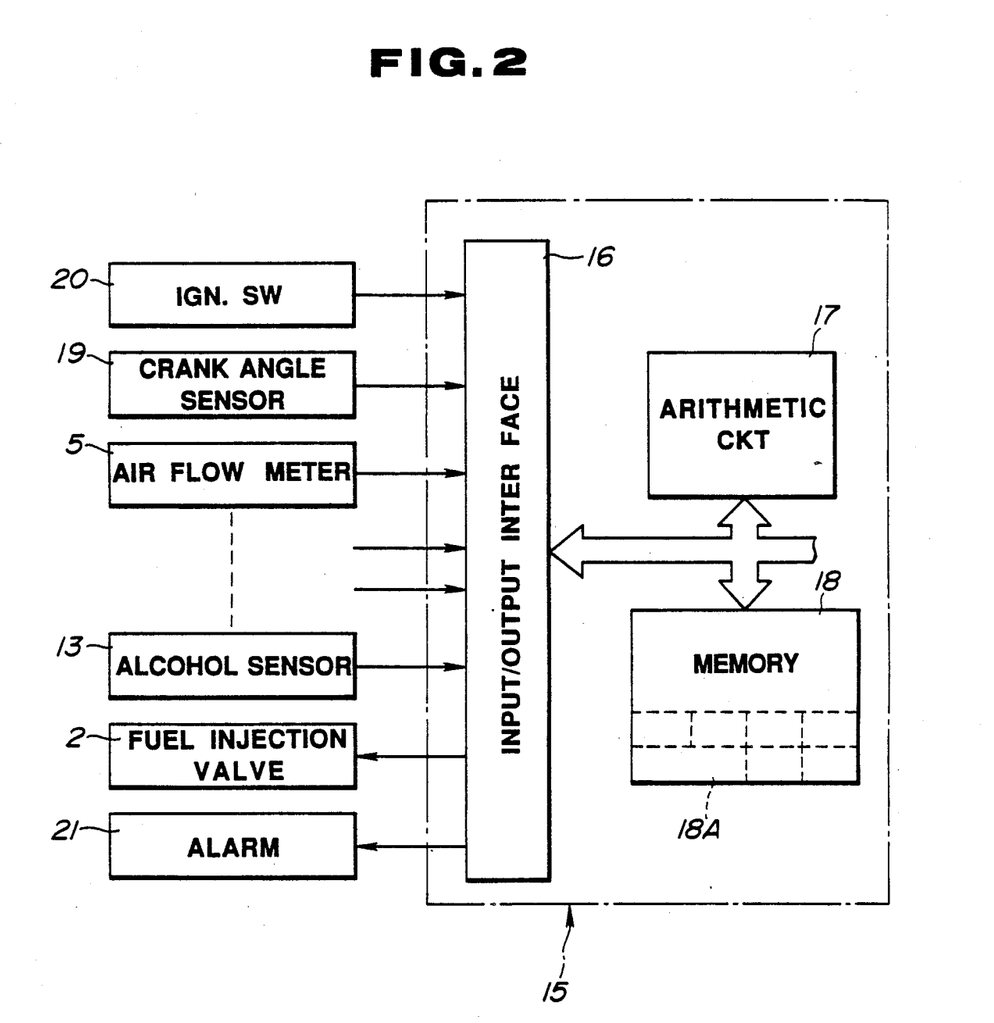
FIG. 2 is a block diagram of the preferred embodiment of a fuel injection control system employed in the internal combustion engine of FIG. 1 and performing fail detection for an alcohol sensor and fail-safe operation in air/fuel ratio feedback control.

FIG. 2 schematically shows the preferred embodiment of a fuel injection control system according to the present invention. The fuel injection control system employs a control unit 15 which comprises a microprocessor comprising an input/output interface circuit 16, an arithmetic circuit 17 and a memory unit 18. The control unit 15 is connected to various sensors, detectors, switches for receiving parameter data representative of the engine driving condition. For example, in the shown embodiment, the control unit 15 is connected to an ignition switch 20, a crank angle sensor 19, the air flow meter 5, the alcohol sensor 13, the oxygen sensor 6a and so forth. In addition to these, an engine coolant temperature sensor, a vehicular battery voltage sensor, an air conditrioner switch and so forth may be connected for providing additional fuel injection control parameter data.

The ignition switch 20 may serve as a main power switch for the fuel injection control system. The crank angle sensor 19 monitors crankshaft angular position to produce a crank reference signal at every predetermined angular position of the crankshaft and a crank position signal at every predetermined angle of angular displacement of the crankshaft. The crank reference signal or the crank position signal is dealt as a parameter representative of engine revolution speed. Process of derivation of the engine speed data on the basis of the crank reference signal or the crank position signal is well known in the art and thus does not necessary to give detailed discussion.

The control unit 15 processes the input data for deriving fuel injection amount and fuel injection timing adapted to the engine driving condition. In general, the fuel injection amount Ti according to the following equation.

$$Ti = Ck \times Tp \times a \times a' \times \text{COEF} + Ts$$

wherein
Ck is a constant set in relation to the alcohol concentration;
Tp is a basic fuel injection amount derived on the basis of the engine load Q represented by the air flow rate indicative signal and the engine speed N derived from the crank reference signal or the crank position signal;
$a$ is an air/fuel ration dependent correction coefficient derived on the basis of the oxygen concentration indicative signal:
$a'$ is a learning correction coefficient for basis air/fuel ratio for correcting the air/fuel ratio dependent correction coefficient $a$;
COEF is a combined correction coefficient of various auxiliary correction factors, such as an engine coolant temperature, an acceleration demand which may be represented by variation rate of the throttle valve;
Ts is a battery voltage compensating correction value.

The control unit 15 thus produces a fuel injection control signal to be supplied to the fuel injection valve 2 for performing fuel injection for the amount Ti. In order to perform fail detection for the alcohol sensor 13, the memory unit 18 is provided memory address 18A specifically adapted to store maximum and minimum voltages $E_1$ and $E_2$ respective which represents upper and lower criteria of the alcohol concentration indicative signal value, and the alcohol concentration indicative signal value E. The alcohol concentration indicative signal value E is cyclically updated at every program cycle. The fresh alcohol concentration indicative signal value E is compared with the maximum and minimum values $E_1$ and $E_2$ for checking whether the alcohol sensor 13 operate in normal state or not. That is, when failure is caused in the alcohol sensor 13, the alcohol concentration indicative signal level tends to become out of the range between the maximum and minimum values $E_1$ and $E_2$. Therefore, by comparing the alcohol concentration indicative signal value E with the maximum and minimum values $E_1$ and $E_2$ and thus detecting the alcohol concentration indicative signal value greater than $E_1$ or smaller than $E_2$. If failure of the alcohol sensor 13 is detected, the control unit 15 output an alarm signal to an alarm unit 21. The alarm unit 21 may comprise an alarm indicator lamp, buzzer and so forth for alarting failure of the alcohol sensor to the driver.

Figure 3:
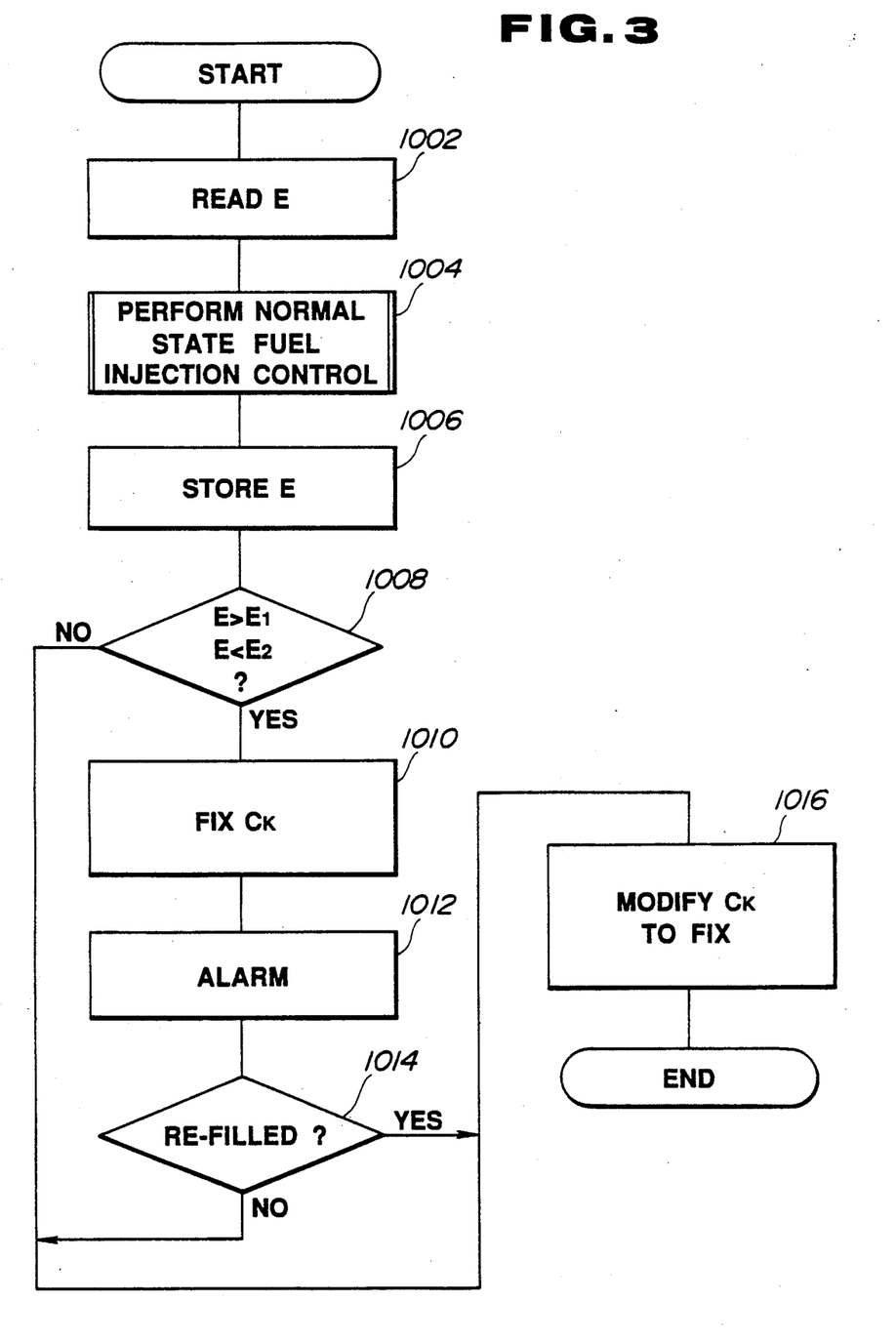
FIG. 3 is a flowchart showing the first preferred process in fail detection and fail-safe operation to be performed by the fuel injection control system of FIG. 2.

The process of fuel injection control to be performed by the control unit 15 will be discussed herebelow with reference to FIG. 3. The shown control routine in FIG. 3 is executed every predetermined timing for principally determining the fuel injection amount Ti. As well, in the shown process, fail detection of detecting failure of the alcohol sensor and fail-safe operation in response to failure of the alcohol sensor is are performed.

Immediately after starting execution, the alcohol concentration indicative signal value E is read out at a step 1002. At a step 1004, various fuel injection control parameters set forth above are read out and processed for deriving the fuel injection amount Ti. At the step 1004, a fuel injection pulse having a duty cycle corresponding to the derived fuel injection amount Ti is output for controlling operation of the fuel injection valve.

After step 1004, the alcohol concentration indicative signal value E is written in the memory address 18A for updating the alcohol concentration indicative data stored therein at a step 1006. Subsequently, at a step 1008, the alcohol concentration indicative signal value E updated is compared with the maximum and minimum values $E_1$ and $E_2$ for checking whether the alcohol sensor 13 operates in normal condition. When the updated value E is smaller than or equal to the maximum value $E_1$ and greater than or equal to the minimum value $E_2$, judgement can be made that the alcohol sensor 13 is in normal state. In such case, process goes END. On the other hand, when the updated value E is greater than the maximum value $E_1$ or smaller than the minimum value $E_2$, judgement is made that failure occurs in the alcohol sensor 13. If failure is detected at the step 1008, the alcohol concentration indicative value E stored in the immediately preceding cycle is read out and the current alcohol concentration indicative value E is replaced with that stored immediately preceding cycle, at a step 1010. Then, at the step 1010, the replaced alcohol concentration indicative value E which is the value obtained immediately before the occurrence of failure of the alcohol sensor is set as the fixed value representative of the alcohol concentration indicative value. Thereafter, the derived Ti is set with the fixed alcohol concentration indicative value derived at the step 1010.

As long as the fuel is not re-filled, the blending rate of the alcohol in the blended fuel will not be changed. Therefore, air/fuel ratio cannot be too rich or too lean even when fixed value of the alcohol concentration indicative value is used for deriving the fuel injection amount Ti.

After setting the fixzed value of the fuel injection amount Ti at the step 1010, an alarm signal is generated at a step 1012 for triggering the alarm unit 21.

For the purpose of fail-safe operation, it may be preferable to give instructions to the driver to re-fill pure gasoline when failure of alcohol sensor occurs. At a step 1014, check is performed whether the pure gasoline is re-filled. Re-filling of the gasoline can be detected by detecting opening of the filler cap or by detecting variation of the fuel level in the tank. If re-filling of gasoline cannot be detected, process directly goes END. On the other hand, if re-filling of gasoline is detected as checked at the step 1014, then minimum fuel injection amount Ti in the normal state fuel injection. Therefore, providing that the driver re-fills gasoline according to the instructions, alcohol concentration is lowered by re-filling gasoline to enable normal state fuel injection control with minimum fuel injection amount so that the vehicle can be driven.

Figure 4:
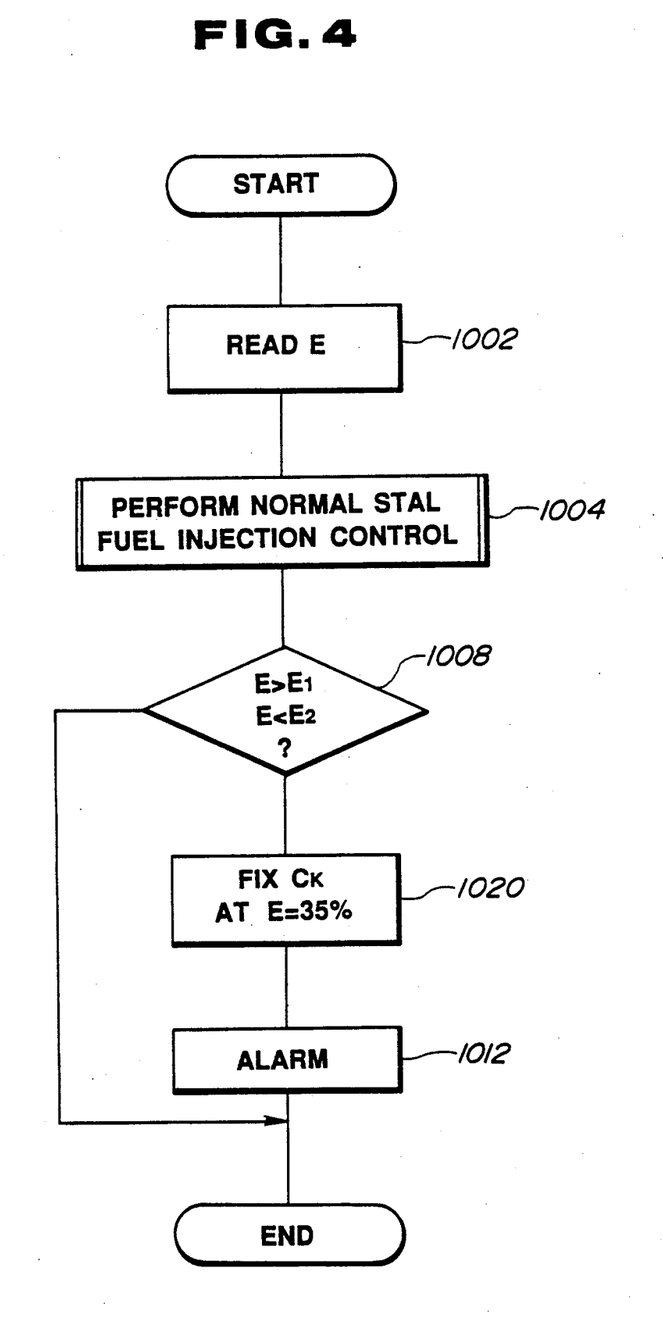
FIG. 4 is a flowchart showing the second preferred process in fail detection and fail-safe operation to be performed by the fuel injection control system of FIG. 2.
Figure 5:
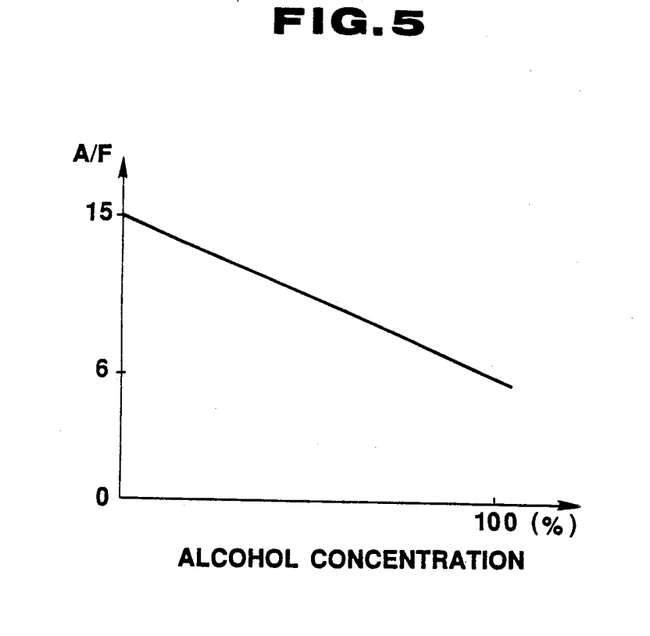
FIG. 5 is a chart showing variation of desirable or target air/fuel ratio in relation to alcohol concentration in the blended fuel.

FIG. 4 shows part of fuel injection control routine modified from that in FIG. 3. In FIG. 4, the process steps doing the identical process to the former routine will be represented by the same laveling and the same step number for neglecting reducdant recitation.

As can be seen, the shown process is differentiated in the step 1020 which is a replacement for the step 1010 of the former routine. Namely, in the shown process, the alcohol concentration indicative value E is fixed at a given ratio, e.g. 35%. Therefore, in the fail-safe mode operation, the fuel injection amount Ti is derived with taking the fixed alcohol concentration indicative value E at the given ratio.

Figure 9:
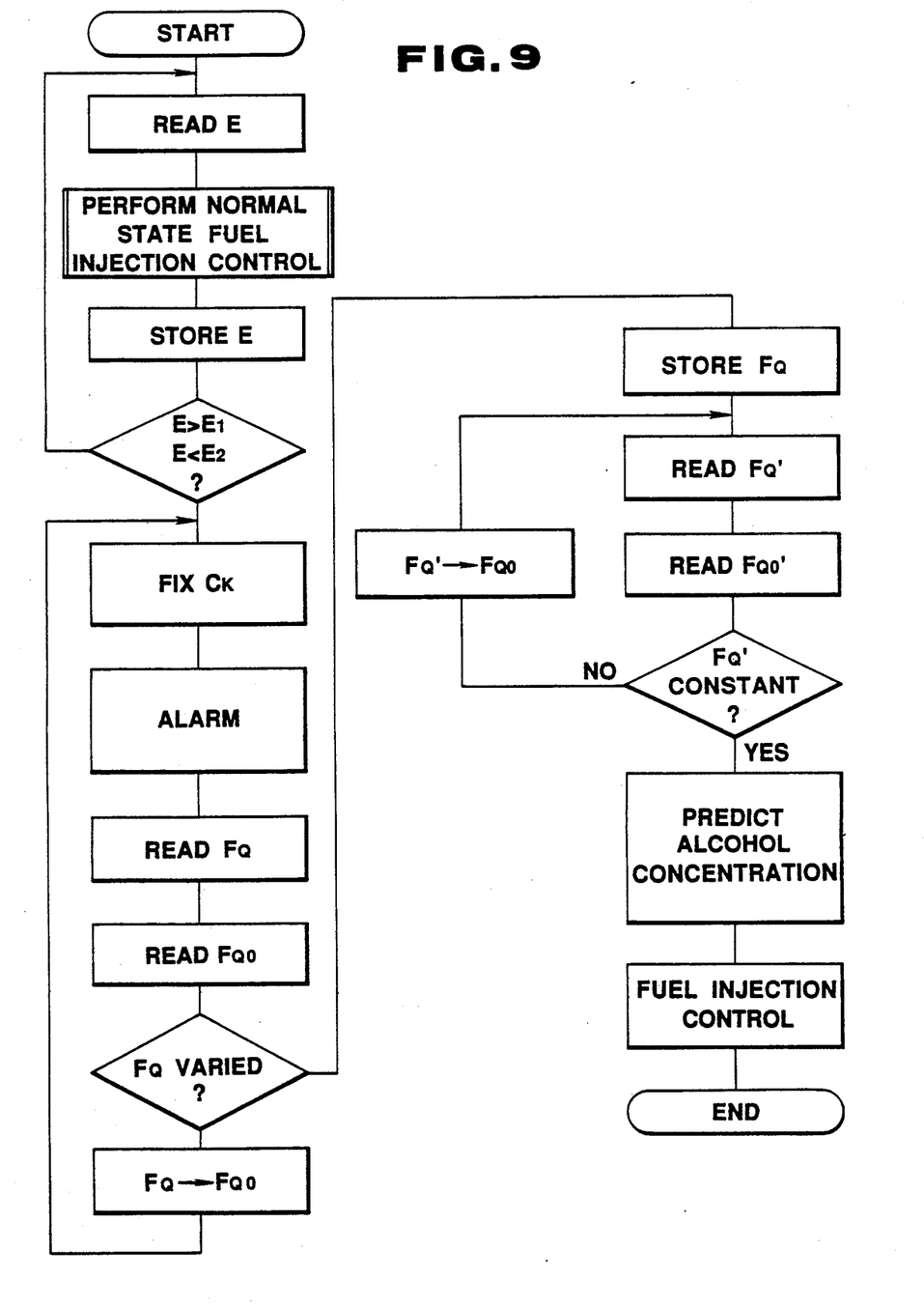
FIG. 9 is a flowchart showing preferred process of fail detection and fail-safe operation to be performed by the fuel injection control system.

FIG. 9 shows another process of fuel injection control to be performed by the fuel injection control system. In the shown process, a predicted alcohol blending ratio is arithmetically derived during fail-safe mode operation. The process through the steps 1002 through 1012 are identical to that in FIG. 3. Therefore, only processes through the steps 1030 to 1050 will be discussed herebelow.

At a step 1030 which is executed after the step 1012, the remaining fuel amount $F_Q$ is read out. At a step 1032, the remaining fuel amount $F_{QO}$ read immediately preceding execution cycle is read out. Then, at a step 1034, $F_Q$ and $F_{QO}$ is compared for detecting whether the remaining fuel level has been changed or not. If not, the value of $F_{QO}$ is updated with the instantaneous $F_Q$ amount at a step 1036 and subsequently, the process goes END. On the other hand, if re-filling of fuel is detected at the step 1036, the remaining fuel level $F_Q$ upon initiation of re-filling is written in the memory as $F_Q$ data at a step 1038. Subsequently, the instantaneous fuel level $F_Q'$ is read out at a step 1040. Then, the remairring fuel amount data $F_{QO}'$ read immediately before is read out at a step 1042. The data values $F_Q'$ and $F_{QO}'$ are compared to detect whether the fuel level is still varying or not at a step 1044. If the fuel level is varying as checked at the step 1042, process goes to a step 1046, in which the $F_{QO}'$ is updated by $F_Q'$ value and then process returns to the step 1040.

On the other hand, if the fuel level is held unchanged as checked at the step 1044, the predicted alcohol blending ratio is arithmetically derived on the basis of the $F_Q$ value and re-filled amount ($F_Q'-F_Q$), at a step 1048. Subsequently, the fuel injection amount Ti is calculated utilizing the predicted blending ratio of alcohol at a step 1050. After process at the step 1050, process goes END.

Figure 10:
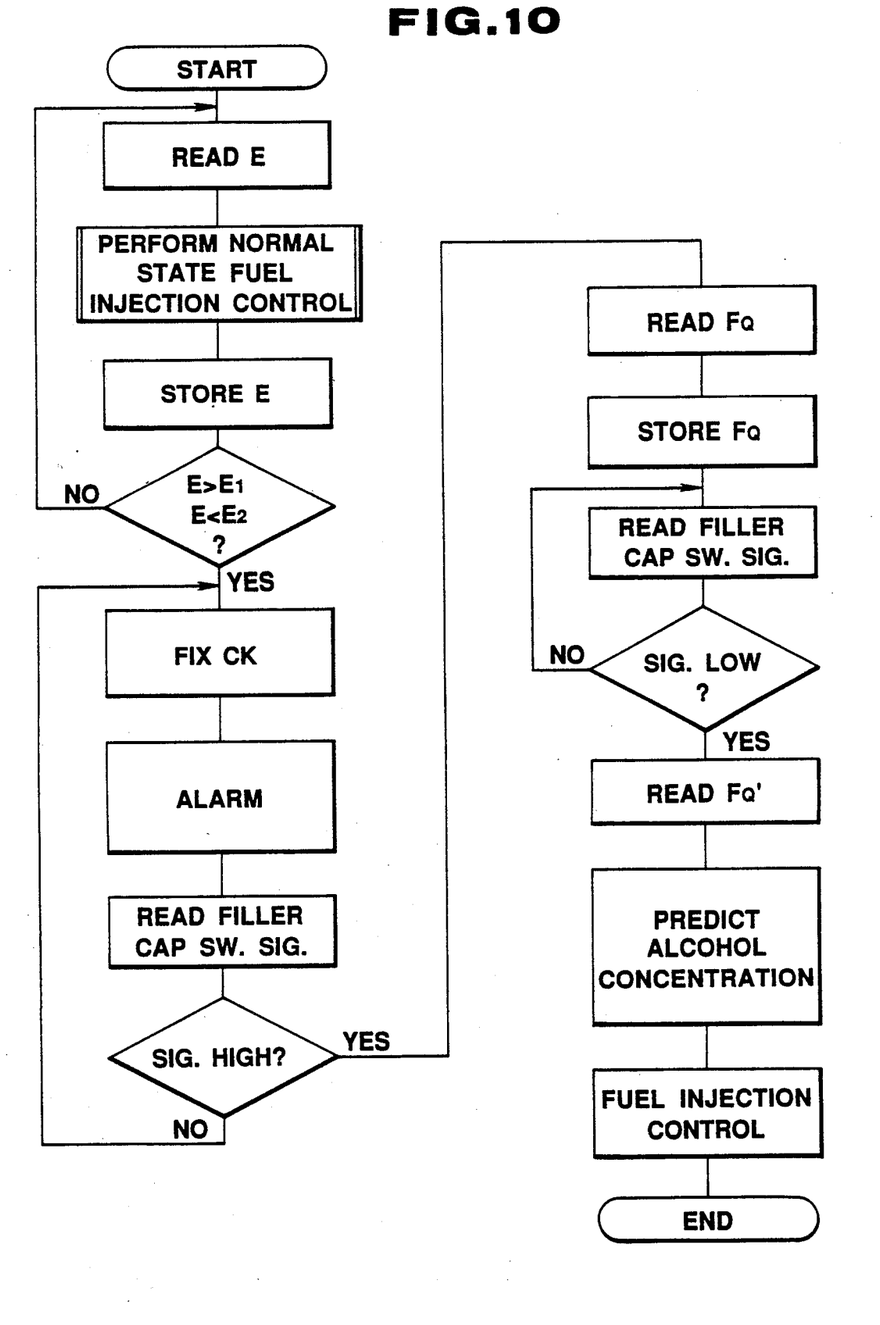
FIG. 10 is a flowchart showing another preferred process of fail detection and fail-safe operation to bb performed by the fuel injection control system.

FIG. 10 shows another modified process of fuel injection control according to the present invention. In the shown process, the steps 1030 to 1044 in FIG. 9 are replaced with the process steps 1060 to 1070.

At a step 1062, check is performed whether the filler cap is opened or not. For enabling this, a filler cap switch which is switched ON when the filler cap is removed from the filler tube opening, may be provided. Therefore, at a step 1060, the filler cap switch signal is read out. Subsequently, the aforementioned check is performed whether the filler cap switch signal level which is maintained HIGH level while the filler cap switch is ON, at a step 1062. If the filler cap switch signal level is LOW, process returns to the step 1010. On the other hand, if the filler cap switch signal as checked at the step 1062 is HIGH level, the remaining fuel amount $F_Q$ is read out at a step 1064 and written in as remaining fuel data immediately before re-filling at a step 1066. Then, at a steps 1068 and 1070, lowering of the filler cap switch signal is checked for detecting termination of re-filling of gasoline. At the steps 1068, the filler cap switch signal level is read out, and at the step 1070, check is performed whether the filler cap switch signal level is LOW. The steps 1068 and 1070 is repeated until LOW level filler cap switch signal is detected. When the LOW level of the filler cap switch signal is detected at the step 1070, process goes to the step 1046.

Figure 11:
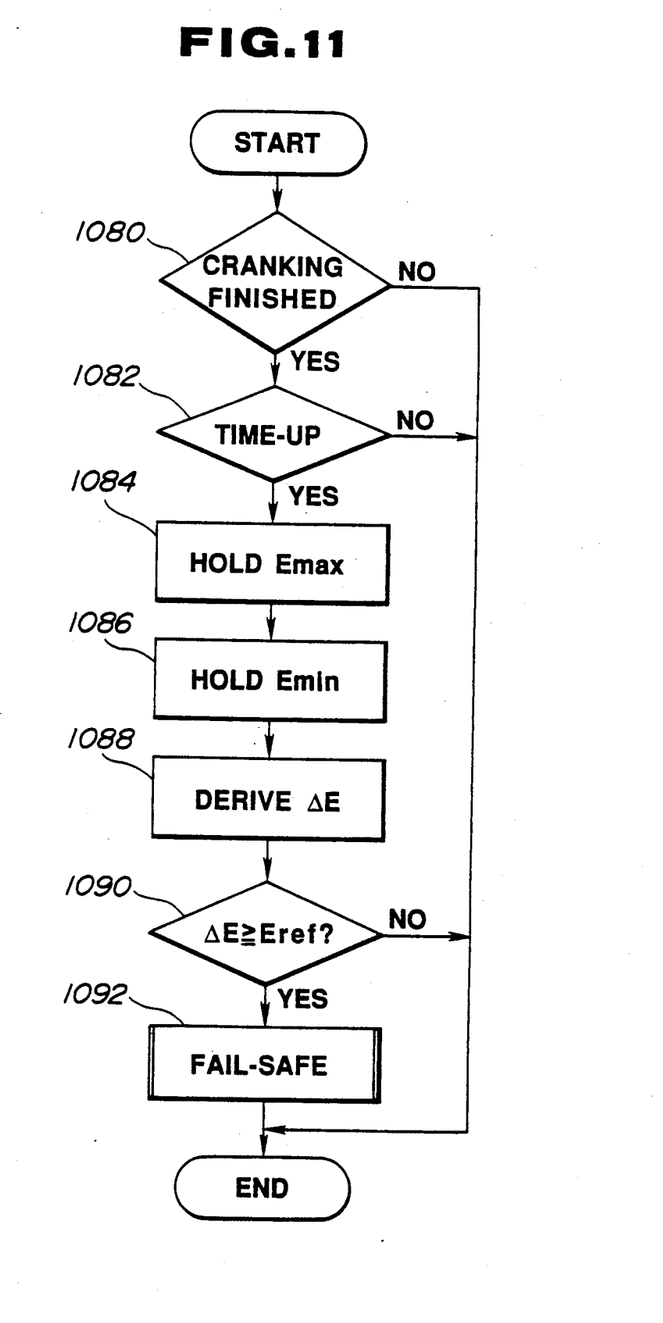
FIG. 11 is a flowchart showing a further process of fail detection and fail-safe operation to be performed by the fuel injection control system according to the present invention.

FIG. 11 shows a further modified process of fuel injection control to be performed by the preferred embodiment of the fuel injection control system according to the invention. In this embodiment, initial check of the alcohol sensor 13 may be performed immediately after cranking for starting up the engine.

Therefore, at a step 1080, check is performed whether cranking is terminated or not. If the engine is in cranking state as checked at the step 1080, process directly goes END. On the other hand, if termination of the engine cranking is detected at the step 1080, an elapsed time after termination of cranking is checked at a step 1082. If the elapsed time checked at the step 1082 is shorter than a predetermined period, then process goes to END and otherwise goes to a step 1084. At the step 1084, the alcohol concentration indicative signal value E is sampled and compared with a previously sampled maximum value $E_{max}$ for upating the maximum value with greater one of the values. At a step 1086, the alcohol concentration indicative signal value E is sampled and compared with a previously sampled minimum value $E_{min}$ for upating the minimum value with smaller one of the values. Then, a difference $\Delta E$ ($=E_{max}-E_{min}$) is derived at a step 1088. Then, the derived difference $\Delta E$ is compared with a predetermined criterion $E_{ref}$ to make judgement whether the alcohol sensor 13 cause failure or not at a step 1090. If failure is detected at the step 1090, fail-safe operation which may be any one of that set forth above, will be initiated at a step 1092.

As can be appreciated herefrom, the present invention is successful in detecting failure of the alcohol sensor for assure initiation of fail-safe operation.

While the present invention has been disclosed in terms of the preferred embodiment in order to facilitate better understanding of the invention, it should be appreciated that the invention can be embodied in various ways without departing from the principle of the invention. Therefore, the invention should be understood to include all possible embodiments and modifications to the shown embodiments which can be embodied without departing from the principle of the invention set out in the appended claims.

What is claimed is:

1. A fail-detection system for a fuel concentration sensor for monitoring concentration of one of a plurality of different types of fuels which are blended to be supplied to an internal combustion engine, which fuel concentration sensor vaires output signal level depending upon the monitored fuel concentration in the blended fuels, said system comprising:

first means for receiving the output signal from said fuel concentration sensor for providing a monitored data associated with monitored fuel concentration;

second means for providing a reference data representative of normal range of the value of said monitored data; and third means for comparing said monitored data with said reference data for detecting abnormality of said fuel concentration sensor when said monitored data is out of a predetermined relationship with said reference data.

2. A fail-detecting system as set forth in claim 1, wherein said first means samples said output signal of said fuel concentration sensor with a given interval as said monitored data, said second means provides first reference data representative of a predetermined allowable maximum value of said monitored data and a second reference data representative of a predetermined allowable minimum value of said monitored data, and said third means detects abnormality of said fuel concentration sensor when said monitored data value is out of an allowable range defined by said first and second reference data.

3. A fail-detecting system as set forth in claim 2, wherein said first reference data is set at a possible monitored data value when the concentration of the fuel to be monitored is 100% and the second reference data is set at a possible monitored data value when the concentration of the fuel to be monitored is 0%.

4. A fail-detecting system as set forth in claim 1, wherein said first means comprises a first peak hold means for sampling and holding upper peak value of said monitored data and a second peak hold circuit means for sampling and holding lower peak value of said monitored data, and said first means includes a difference deriving means for deriving a difference data of said upper peak value and said lower peak value, said second means provides said reference data representative of an allowable maximum difference value, and said third means compares said difference data with said reference data to detect abnormality of said fuel concentration sensor when the difference data is greater than said reference data.

5. A fail-detection system for a fuel concentration sensor for monitoring concentration of one of a plurality of different types of fuels which are blended to be supplied to an internal combustion engine, which fuel concentration sensor vaires output signal level depending upon the monitored fuel concentration in the blended fuels, said system comprising:

first means sampling said output signal of said fuel concentration sensor with a given interval as said monitored data;

second means providing first reference data representative of a predetermined allowable maximum value of said monitored data and a second reference data representative of a predetermined allowable minimum value of said monitored data; and third means detecting abnormality of said fuel concentration sensor when said monitored data value is out of an allowable range defined by said first and second reference data.

6. A fail-detecting system as set forth in claim 5, wherein said first reference data is set at a possible monitored data value when the concentration of the fuel to be monitored is 100% and the second reference data is set at a possible monitored data value when the concentration of the fuel to be monitored is 0%.

7. A fail-detection system for a fuel concentration sensor for monitoring concentration of one of a plurality of different types of fuels which are blended to be supplied to an internal combustion engine, which fuel concentration sensor varies output signal level depending upon the monitored fuel concentration in the blended fuels, said system comprising:

first means including a first peak hold means for sampling and holding upper peak value of said monitored data and a second peak hold circuit means for sampling and holding lower peak value of said monitored data, and a difference deriving means for deriving a difference data of said upper peak value and said lower peak value;

second means provides said reference data representative of an allowable maximum difference value; and third means compares said difference data with said reference data to detect abnormality of said fuel concentration sensor when the difference data is greater than said reference data.

8. A fail-detecting system as set forth in claim 7, which is active at initial stage of engine driving after a predetermined period of time from termination of engine cranking.

9. A fuel injection control system for an internal combustion engine for which a blended fuel composed of mutually different type of plurality of fuel is supplied for performing combustion, comprising:

a fuel injection system for injecting controlled amount of the blended fuel to an induction system of said engine for forming an air/fuel mixture to be combustioned in a combustion chamber of the engine;

first means for monitoring basic fuel injection control parameter for deriving a basic fuel injection amount on the basis thereof;

second means for monitoring preselected fuel injection amount correcting parameter for deriving a correction value for correcting said basic fuel injection amount;

third means for monitoring blending ratio of selected one of fuels in said blended fuel for deriving a blending ratio dependent correction value for correcting said basic fuel injection amount based thereon, said third means including a sensor for monitoring concentration of the selected one of fuels;

fourth means for detecting abnormality of said sensor, including a monitoring data providing means for receiving the output signal from said fuel concentration sensor for providing a monitored data associated with monitored fuel concentration, a reference data providing means for providing a reference data representative of normal range of the value of said monitored data, and an abnormality detecting means for comparing said monitored data with said reference data for detecting abnormality of said fuel concentration sensor when said monitored data is out of a predetermined relationship with said reference data; and fifth means responsive to said fourth means detecting abnormality of said sensor for switching operational mode of said third means from normal mode in which the blending ratio dependent correction value on the basis of the monitored blending ratio, to a fail-safe mode in which said blending ratio dependent correction value is fixed at a given constant value.

10. A fuel injection control system as set forth in claim 9, wherein said first means samples said output signal of said fuel concentration sensor with a given interval as said monitored data, said second means provides first reference data representative of a predetermined allowable maximum value of said monitored data and a second reference data representative of a predetermined allowable minimum value of said monitored data, and said third means detects abnormality of said fuel concentration sensor when said monitored data value is out of an allowable range defined by said first and second reference data.

11. A fuel injection control system as set forth in claim 10, wherein said first reference data is set at a possible monitored data value when the concentration of the fuel to be monitored is 100% and the second reference data is set at a possible monitored data value when the concentration of the fuel to be monitored is 0%.

12. A fuel injection control system as set forth in claim 9, wherein said first means comprises a first peak hold means for sampling and holding upper peak value of said monitored data and a second peak hold circuit means for sampling and holding lower peak value of said monitored data, and said first means includes a difference deriving means for deriving a difference data of said upper peak value and said lower peak value, said second means provides said reference data representative of an allowable maximum difference value, and said third means compares said difference data with said reference data to detect abnormality of said fuel concentration sensor when the difference data is greater than said reference data.

13. A fuel injection control system as set forth in claim 9, which further comprises sixth means for detecting re-filling of fuel and said third means is responsive to said sixth means detecting re-filling of fuel for modifying said blending ratio dependent correction value in said fail-safe mode.

14. A fuel injection control system as set forth in claim 13, wherein said sixth means monitors fuel level in a fuel tank for detecting re-filling of fuel on the basis of variation of the fuel level.

15. A fuel injection control system as set forth in claim 13, wherein said sixth means detects opening of a fuel filler cap for detecting re-filling of fuel.

16. A fuel injection control system as set forth in claim 13, wherein said third means modifies said blending ratio depent correction value in said fail-safe mode in a magnitude variable depending upon a prediction of variation of blending ratio by re-filling of fuel.

* * * * *